US012733565B2

(12) United States Patent
Eviston

(10) Patent No.: US 12,733,565 B2
(45) **Date of Patent: *Sep. 15, 2026**

(54) METHOD AND DEVICE FOR DELIVERING VIABLE MICROORGANISMS IN SEED LUBRICANT TO SEED SUPPLY

(71) Applicant: Meristem Crop Performance Group, LLC, Powell, OH (US)

(72) Inventor: Mitchell Eviston, Woodbury, MN (US)

(73) Assignee: Meristem Crop Performance Group, LLC, Powell, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/315,398

(22) Filed: Aug. 29, 2025

(65) Prior Publication Data

US 2026/0053082 A1 Feb. 26, 2026

Related U.S. Application Data

(63) Continuation of application No. 18/503,899, filed on Nov. 7, 2023, now Pat. No. 12,402,556, which is a (Continued)

(51) Int. Cl.

*A01C 1/06* (2006.01)
*A01C 1/08* (2006.01)
*C12N 1/20* (2006.01)

(52) U.S. Cl.

CPC ................. *A01C 1/06* (2013.01); *A01C 1/08* (2013.01); *C12N 1/20* (2013.01)

(58) Field of Classification Search

CPC .. A01C 15/02; A01C 7/06; A01C 1/08; A01C 1/06

See application file for complete search history.

(56) References Cited

U.S. PATENT DOCUMENTS 3,068,154 A 12/1962 Majors
3,156,369 A 11/1964 Bowes et al.
(Continued)

FOREIGN PATENT DOCUMENTS

CN 207956518 U 10/2018
CN 113879693 A 1/2022
(Continued)

OTHER PUBLICATIONS

"Capods—Pre-Filled Unit Dose Caps," Lucas Packaging Group, Mar. 3, 2021, retrieved from https://lucaspackaging.com/capod/ [accessed on Apr. 16, 2025].

(Continued)

*Primary Examiner* — Monica L Perry

(74) *Attorney, Agent, or Firm* — Foley & Lardner LLP

(57) ABSTRACT

A package 10 comprises a main body 12 for containing a seed lubricant; and a chamber 24 for retaining microorganisms in a viable state, wherein the main body 12 and the chamber 24 are separated by a disruptable dividing member 32, and further comprising a mechanism for disrupting the dividing member 32 such that the seed lubricant and the microorganisms may be blended just prior to deployment on a seed planter and wherein the main body 12, the chamber 24 and the disrupting member form an integral package suitable for providing the blend of seed lubricant and viable microorganisms to seeds in a seed planter.

20 Claims, 4 Drawing Sheets

Related U.S. Application Data continuation of application No. 18/197,578, filed on May 15, 2023, now Pat. No. 11,812,685, which is a continuation of application No. PCT/US2023/012628, filed on Feb. 8, 2023.

(60) Provisional application No. 63/434,588, filed on Dec. 22, 2022.

(56) References Cited

U.S. PATENT DOCUMENTS

| | | | |
|---|---|---|---|
| 3,406,872 A | 10/1968 | Fiquet et al. | |
| 3,504,376 A | 3/1970 | Bednar et al. | |
| 3,715,189 A | 2/1973 | Nighohossian et al. | |
| 3,968,872 A | 7/1976 | Cavazza | |
| 4,103,772 A | 8/1978 | Wiegner | |
| 4,195,730 A | 4/1980 | Hunt | |
| 4,283,498 A | 8/1981 | Schlesinger | |
| 4,306,357 A | 12/1981 | Villarejos | |
| 4,640,895 A | 2/1987 | Davis | |
| 4,785,931 A | 11/1988 | Weir et al. | |
| 4,903,865 A | 2/1990 | Janowitz | |
| 5,431,276 A | 7/1995 | Lialin | |
| 5,507,133 A | 4/1996 | Singleton et al. | |
| 5,772,017 A | 6/1998 | Kang | |
| 5,979,647 A | 11/1999 | Han | |
| 6,148,996 A | 11/2000 | Morini | |
| 6,959,839 B2 | 11/2005 | Roth et al. | |
| 6,976,578 B1 | 12/2005 | Kenihan | |
| 7,607,549 B2 | 10/2009 | Morini | |
| 8,297,456 B1 | 10/2012 | Anderson | |
| 8,308,075 B2 | 11/2012 | Eastin et al. | |
| 8,443,970 B2 | 5/2013 | Coon | |
| 8,453,834 B2 | 6/2013 | Porter | |
| 8,584,840 B2 | 11/2013 | Kim | |
| 8,770,399 B2 | 7/2014 | Hjalmarsson | |
| 9,174,881 B2 | 11/2015 | Cimaglio et al. | |
| 9,260,740 B2 | 2/2016 | Sharpin | |
| 10,065,775 B2 | 9/2018 | Estes et al. | |
| 10,285,908 B2 | 5/2019 | Mittal et al. | |
| 10,369,078 B2 | 8/2019 | Bhargava et al. | |
| 10,774,298 B2 | 9/2020 | Caldwell et al. | |
| 12,060,199 B2 * | 8/2024 | Den Boer | B65D 47/10 |
| 12,091,222 B2 * | 9/2024 | den Boer | B05B 11/0056 |
| 12,116,173 B2 * | 10/2024 | den Boer | B05B 11/0097 |
| 12,402,557 B2 * | 9/2025 | Eviston | A01C 1/06 |
| 12,546,101 B2 * | 2/2026 | Rice | E03D 9/022 |
| 2006/0154363 A1 | 7/2006 | Horn | |
| 2006/0236925 A1 | 10/2006 | Lund | |
| 2008/0142473 A1 | 6/2008 | Cho | |
| 2008/0293156 A1 | 11/2008 | Smith | |
| 2008/0314775 A1 | 12/2008 | Owoc | |
| 2009/0048128 A1 | 2/2009 | Custis et al. | |
| 2010/0044377 A1 | 2/2010 | Porter | |
| 2011/0049081 A1 | 3/2011 | Bourguignon | |
| 2012/0061421 A1 | 3/2012 | Roth et al. | |
| 2013/0139703 A1 | 6/2013 | Hogarth | |
| 2015/0360844 A1 | 12/2015 | Frieden | |
| 2016/0053218 A1 | 2/2016 | Caldwell et al. | |
| 2018/0148220 A1 | 5/2018 | Kincaid | |
| 2018/0177192 A1 | 6/2018 | Johnson | |
| 2020/0347336 A1 | 11/2020 | Caldwell et al. | |
| 2021/0171254 A1 | 6/2021 | Love et al. | |
| 2024/0206368 A1 | 6/2024 | Eviston | |

FOREIGN PATENT DOCUMENTS

| | | |
|---|---|---|
| CN | 215476947 U | 1/2022 |
| JP | 3002282 U | 9/1994 |
| KR | 101818944 B1 | 2/2018 |
| WO | WO-2018/098254 A1 | 5/2018 |
| WO | WO-2018/109018 A1 | 6/2018 |

OTHER PUBLICATIONS

"Fresh Beverages International—Shinsen Cap," No Time Like the Present, Apr. 7, 2017, retrieved from https://ntltp.com/fresh-beverages-international/ [accessed on Apr. 16, 2025].

Bouckley, Ben, "'Unique' bottle dosing and dispensing cap boosts brand visibility: Tap the Cap," Beverage Daily, Oct. 23, 2012, retrieved from https://www.beveragedaily.com/Article/2012/10/24/Unique-bottle-dosing-and-dispensing-cap-boosts-brand-visibility-Tap-the-Cap/ [accessed on Apr. 16, 2025].

International Preliminary Report on Patentability Transmittal on PCT PCT/US2023/012628 DTD Jul. 3, 2025.

International Search Report on PCT PCT/US2023/012628 DTD Sep. 14, 2023.

International Search Report on PCT PCT/US2025/016460 DTD Jun. 2, 2025.

MX Office Action on MX/a/2025/007427 DTD Jun. 24, 2025.

Steeman, Anton, "Innovative Dispensing Bottle Caps for Sensitive Vitamins," Best in Packaging, May 29, 2009, retrieved from https://bestinpackaging.wordpress.com/2009/05/29/innovative-dispensing-bottle-caps-for-sensitive-vitamins/ [accessed on Apr. 16, 2025].

* cited by examiner 14
34
24
24

14
34
20
42

METHOD AND DEVICE FOR DELIVERING VIABLE MICROORGANISMS IN SEED LUBRICANT TO SEED SUPPLY

CROSS-REFERENCE TO RELATED APPLICATION

This application is a Continuation of U.S. patent application Ser. No. 18/503,899 filed Nov. 7, 2023 which is a Continuation of U.S. patent application Ser. No. 18/197,578, filed May 15, 2023 which is a Bypass-Continuation application of International Application No. PCT/US2023/012628, filed Feb. 8, 2023, which claims priority to U.S. Provisional patent application Ser. No. 63/434,588, filed Dec. 22, 2022, the contents of which are hereby incorporated by reference in their entirety.

BACKGROUND

The present invention relates to the storing and delivery of viable microorganisms to seeds and more specifically to a packaging for the storage and delivery of viable microorganisms to seeds via the lubricant used in planting.

Farmers use a seed lubricant when planting corn, soybeans, cotton, sorghum, and/or other crops. Talc and graphite lubricant are used as an effective vehicle for lubricating seeds in a seeder and/or planter to eliminate bridging of the seed in the hopper during the planting process. The lubricant can also be used to deliver microbes/spores with the seed to the earth. However, microbes cannot survive long-term in the lubricant, thus they cannot be premixed with the seed. Also mixing microbes/spores in the field with the lubricant under questionable weather conditions that often occur in the spring is difficult, and may affect the viability of the microbes.

SUMMARY

An aspect of the present disclosure relates to a package comprising a main body for containing a seed lubricant; and a chamber for retaining microorganisms in a viable state, wherein the main body and the chamber are separated by a disruptable dividing member, and further comprising a mechanism for disrupting the dividing member such that the seed lubricant and the microorganisms may be blended just prior to deployment on a seed planter and wherein the main body, the chamber and the disrupting member form an integral package suitable for providing the blend of seed lubricant and viable microorganisms to seeds in a seed planter.

The dividing member is tearable, frangible, puncturable, rupturable, dissolvable, movable or combinations thereof.

The disrupting member is manually actuated to disrupt the dividing member.

The package further comprises a handle for transport of the package.

The seed lubricant comprises a blend of talc and graphite.

In one or more embodiments, the chamber for retaining microorganisms is a first chamber and the package comprising at least a second chamber for retaining microorganisms and the second chamber also separated from the main body by a disruptable dividing member.

Another aspect of the present disclosure relates to a package for delivering viable microorganisms to a seeder and/or planter. The package has a lid portion comprising a first chamber, the first chamber comprising microorganisms therein; a body portion comprising a second chamber, wherein the lid portion is attachable to the body portion such that the first chamber transcends the lid portion and extends into the second chamber; and a dividing member separating the microorganisms in the first chamber from the second chamber. Disrupting the dividing member allows release of the microorganisms into the second chamber. The lid portion may be removable from the body portion.

In one or more embodiments, the first chamber is sealed.

The dividing member is tearable, frangible, puncturable, rupturable, dissolvable, movable or combinations thereof.

The first chamber further comprises a deployment mechanism configured to disrupt the dividing member to release the microorganisms from the first chamber into the second chamber.

The deployment mechanism comprises a push-button accessible from a top of the first chamber and operably connected to a plunger within the first chamber wherein the plunger is configured to tear, puncture, rupture, dissolve, or move the dividing member or combinations thereof.

The second chamber comprises seed flow lubricant therein.

The seed flow lubricant is a blend of talc and graphite lubricant.

In one or more embodiments, the package comprises a plurality of first chambers each comprising microorganisms.

In one or more embodiments, the dividing member comprises one or more surfaces, walls, or floor of the first chamber.

The lid portion is removably connectable to the second chamber to close off the second chamber. One or a plurality of first chambers are affixed or integrated into the lid portion and are thus removable from the second chamber by removal of the lid.

Yet another aspect of the present disclosure relates to a method of delivering viable microorganisms to a seeder and/or planter by providing a package comprising a first chamber containing microbes therein and a second chamber containing a seed lubricant therein and a disruptable dividing member separating the first chamber from the second chamber; disrupting the dividing member separating a first chamber from a second chamber and thereby introducing the microorganisms into the second chamber wherein the microorganisms are mixed with the seed lubricant to form a microbial lubricant mixture; and applying the viable microbial lubricant mixture to seed.

Pushing a top portion of the first chamber moves a plunger inside the first chamber to disrupt the dividing member.

Transporting and storing the package with the microbes separated from the seed lubricant and waiting to disrupt the dividing member and mixing the microbes and seed lubricant until a time for lubricating the seeds in a seed box or planter thereby providing a mixture of viable microorganisms and seed lubricant.

Further, in one or more embodiments, the method allows for waiting one or more days before disrupting the dividing member separating a first chamber from a second chamber and mixing the microorganisms and seed lubricant.

In one or more embodiments the method comprising waiting one or more months before disrupting the dividing member separating a first chamber from a second chamber and mixing the microorganisms and seed lubricant.

Yet another aspect of the present disclosure relates to a device for providing a seed flow lubricant and viable microorganism mixture to a seed supply. The device has a main body having a chamber configured for holding a supply of seed flow lubricant therein; a lid for the main body and supporting a plurality of capsules thereon, each capsule configured for holding a supply of microorganisms therein; and a deployment mechanism configured to release the supply of microorganisms from each capsule into the chamber holding the supply of seed flow lubricant therein.

The lid supports the plurality of capsules with a first portion of each capsule extending from a first side of the lid and into the chamber holding the supply of seed flow lubricant therein and a second portion of each capsule extending from a second side of the lid such that the deployment mechanism is provided outside of the device.

Each of the plurality of capsules is provided with a deployment mechanism positioned on the second portion of each capsule and wherein the deployment mechanism is configured to tear, puncture, rupture, dissolve, or move one or more surfaces of the first portion of each capsule.

In one or more embodiments, the lid further comprises one or more recessed surfaces for holding accessories or tools for transferring seed flow lubricant or seed flow lubricant mixed with viable microorganisms from the device to a planter box or seed hopper for lubricating the seeds.

DETAILED DESCRIPTION

Figure 1:
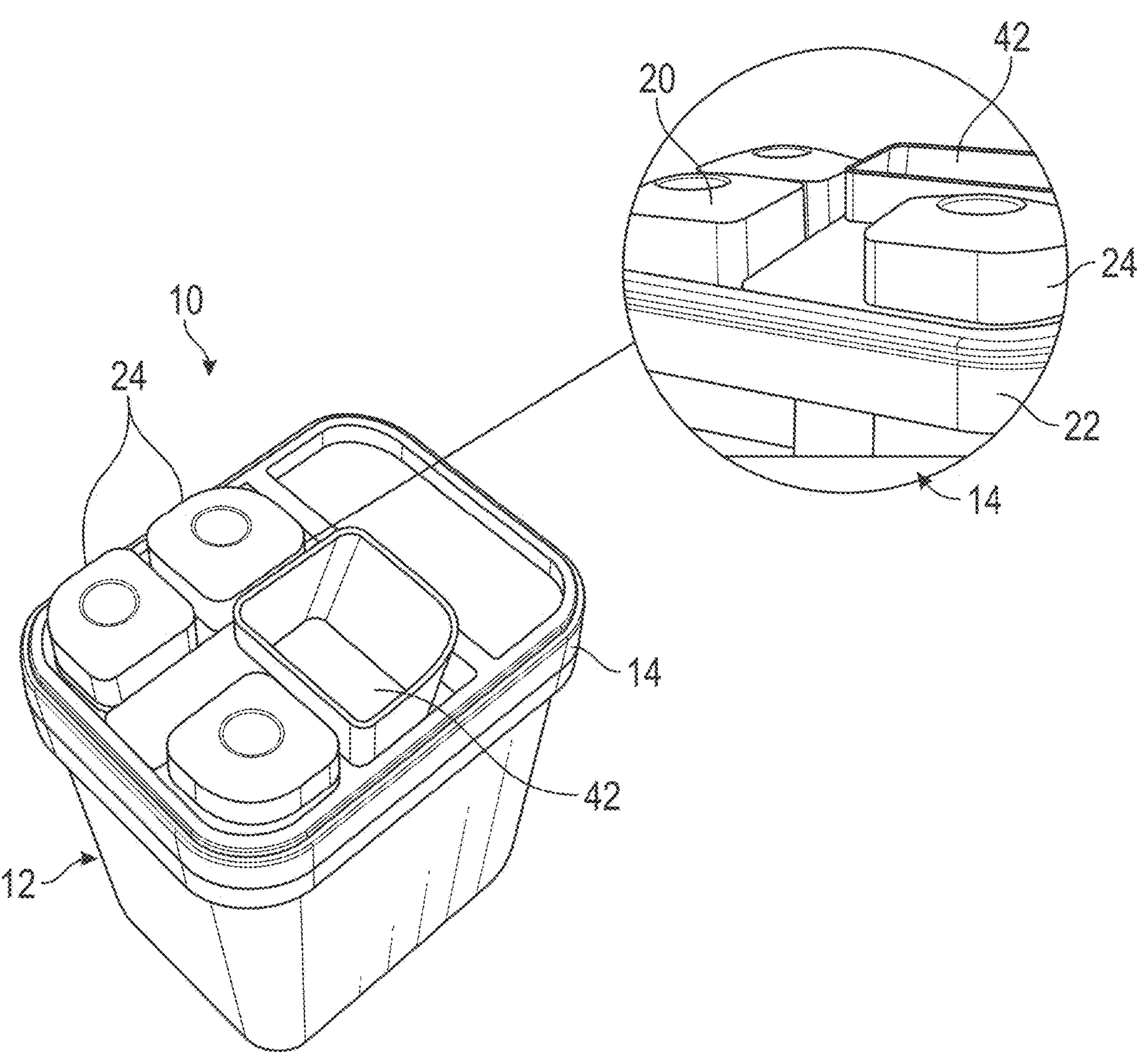
FIG. 1 is perspective view of a package for delivery of viable microorganisms according to one or more embodiments herein.
Figure 3:
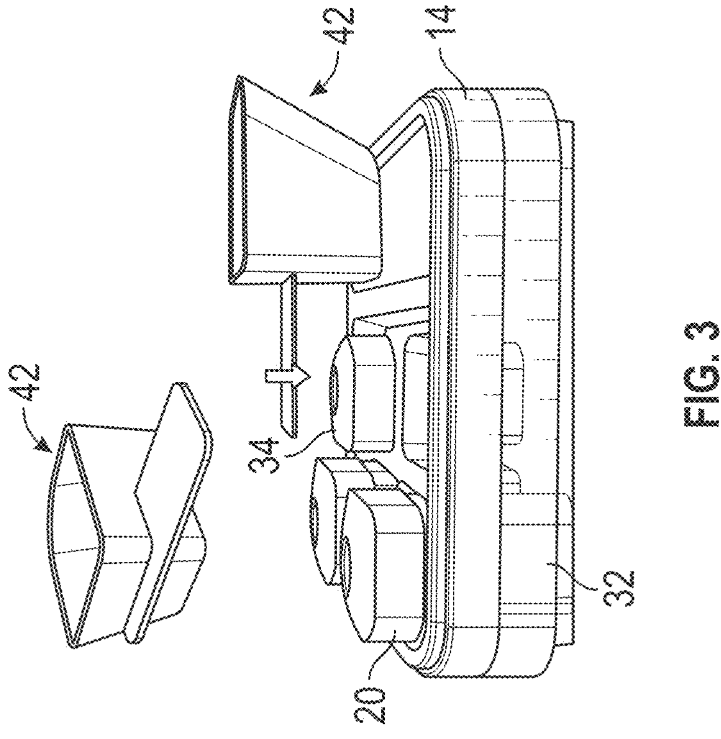
FIG. 3 is a side view of a lid and capsule configuration of the package.
Figure 2:
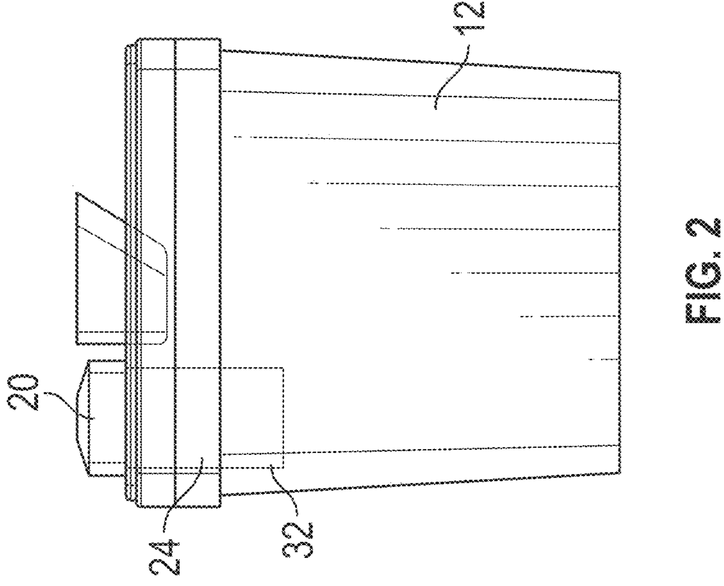
FIG. 2 is a side view of the package showing illustrating the capsule for holding microorganisms.
Figures 4, 5:
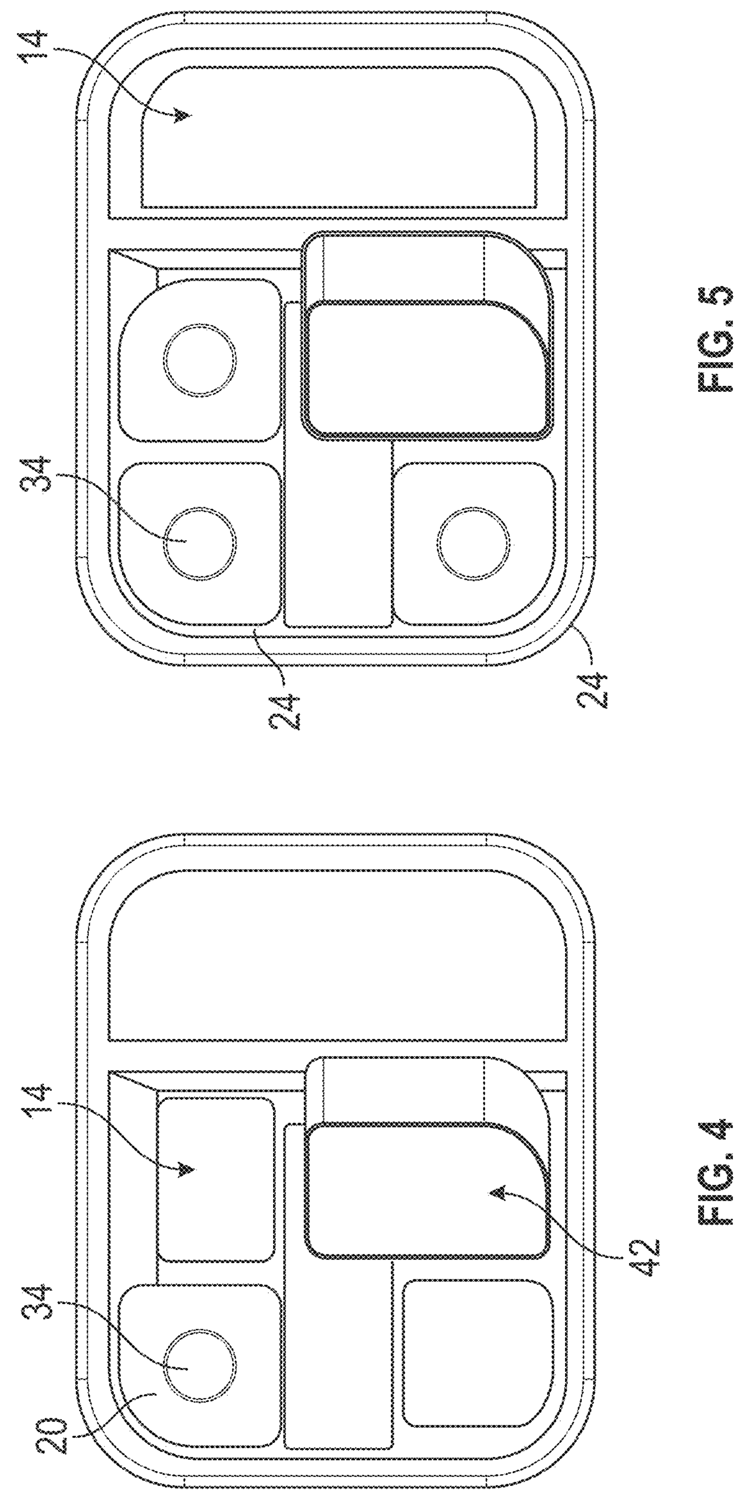
FIGS. 4 and 5 are top views of the lid with one or more capsules.

A device for delivery of viable biological agents and/or microorganisms with seeds through a hopper box during planting is described herein. The device provides a sealed, closed environment that keeps the biological agents viable and disperses the biological agents into a medium to be applied to seeds through a hopper box as described herein. The medium may be a seed lubricant such as a talc and/or graphite based lubricant.

The device described herein is a housing that supports anywhere from one to six or more sealed capsules therein. The capsules contain one or more biological agents, or a combination of microorganisons, biological agents including, fungicides, insecticides, nematicides, plant growth regulators, fertilizers, and micronutrients therein. The capsules are then selectively deployed by a user into a chamber in the device containing the medium, such as the seed lubricant. The seed lubricant and seed are then dispersed through a hopper box when planting.

The device comprises a container portion with a lid. The capsules may be supported on and/or accessed by the lid, whereas the container portion comprises a reservoir for the seed lubricant adjacent to the sealed capsules. The lid may be removably connected to the container portion. The capsules may then also be integral with the lid or removably insertable with respect to one or more openings in the lid. Integral for purposes of this application means consisting or composed of parts that together constitute a whole, and as applied herein means that the components of the package of this disclosure comprise a unitary package that separates and protects the seed lubricant and microorganisms to ensure viability of the microorganisms upon and until release into seed lubricant for application of the blend of the seed lubricant and microorganisms into the seed hopper of the planter.

The lid comprises the one or more capsule holding areas which support one or more capsules, such that the lid holds the capsule(s). For example, the lid may hold one or more capsules with at least a portion of the capsule extending into the container portion of the device as the lid is placed on the container and thus positioned below the lid. At least one surface of the capsule is exposed on an opposite side of the lid, such as on top of the lid. The one or more capsules are then carried by the device. However, the capsules remain sealed until a user breaks the seal of one or more of the capsules of the device, allowing the biological agent therein to enter the reservoir and mix with the seed lubricant. The device can then be shaken or agitated to mix the deployed contents of the capsules into the seed lubricant reservoir.

The device lid may further comprise one or more recessed surfaces for storage of additional items or components, such as a scoop, tools, instructions or accessories. The lid also comprises a perimeter configured to rest on an opening of the device so that the lid covers the container portion. When capsules are held by the lid and the lid is coupled to the container portion, the interior of the container portion is substantially covered and enclosed.

Each of the one or more capsules may be considered a chamber which comprises a cover or capsule lid and which may be provided with one or more deployment mechanisms configured to rupture a floor or wall which acts as a dividing member separating the contents of the capsule chamber from the reservoir chamber. The one or more deployment mechanisms may additionally or alternatively rupture or break any other seal of the capsule chamber, thus deploying the contents of the capsule into the reservoir. For example, the capsule chamber may be configured with the capsule lid having a surface that can be depressed to deploy the contents of the capsule though or around the dividing member of the capsule chamber to the lubricant reservoir. The capsule lid may be a push-activated lid capsule, where manual pressure from pushing a surface of the lid disrupts the integrity of the dividing member such as a wall or floor of the capsule. The disruption may be from a blunt or a sharp element in the capsule being displaced to displace or puncture the wall or floor of the capsule and/or may comprise a change in the pressurization of the capsule thus rupturing or displacing the wall(s) and/or floor of the capsule. Other mechanisms include a plunger mechanism, puncture mechanism, slice mechanism, tearing mechanism, pealing mechanism, air pressure mechanism to effectively pop the capsule or combinations thereof.

The one or more capsules are chambers retained proximate the reservoir with a portion of the capsule positioned within the container portion. The lid of the device may have one or more apertures for holding the one or more capsules with the capsule lid or other capsule surface exposed to a user. The lid may also have surfaces to securely hold the capsule while the capsule cover or lid is pushed or otherwise as the capsule contents are deployed. Thus, the opening of the sealed capsule allows for the biological agent in the capsule to be released into an interior cavity of the container portion such as the reservoir.

Optional shaking or agitation of the device itself aids in further mixing and/or combining the biological agent from one or more capsules with the seed lubricant in the reservoir.

After the capsule contents have been deployed, the device lid may be removed so the mixture can be applied to seeds in a seed box, scooped into a seed hopper with a scoop provided with the device and/or otherwise applied to the seeds just prior to planting as a preparation step immediately preceding planting and/or concurrently with planting.

As the device allows for the use of the sealed capsule(s) for the biological agent(s) where the contents of the capsules remain viable for extended periods of time and segregated from the container portion of the device and any contents therein, the device prevents inadvertent mixing of components and allows an assembled device with one or more sealed capsules and optionally with a seed lubricant in the reservoir to be stored long-term while retaining the viability of the biological agent sealed therein. For example, the device may be stored for days, weeks or even months before the contents are mixed.

The biological agent described herein generally refers to one or more microorganisms and/or spores beneficial to the seed, soil, plant, or combinations thereof. The biological agent may comprise beneficial microbes, inoculants, nutrients, as well as fungicides, insecticides, nematicides, plant growth regulators, fertilizers, micronutrients and the like as well as combinations thereof. Both natural and synthetic biological agents are contemplated and within the scope of this disclosure. For example, the biological agent may comprise a synthetic fungicide such as an acylalanine fungicide with systemic function. Example of which include but are not limited to Metalaxyl (methyl N-(methoxyacetyl)-N-(2,6-xylyl)-DL-alaninate).

The seed lubricant described herein may be a seed flow lubricant including but not limited to a lubricant comprising a mixture of talc and graphite. Additional and alternative seed lubricants may be used in the reservoir of the device according to one or more embodiments described herein.

The device may be comprised of a material suitable for long- and short-term storage of seed lubricant. For example, the device including one or both of the container portion and lid may be constructed of a metal, hard plastic material, composite materials, or combinations thereof. One or both of the container portion and/or lid may be transparent, semi-transparent or translucent or have an area that is transparent, semi-transparent or translucent so that the contents in the container may be seen or a quantity therein observed without removing the lid from the container portion.

The size and overall dimensions of the device may vary by end use and quantity needed. The device may be configured with dimensions and a corresponding lid to support one or more capsules therein, including up to six or more capsules. The container portion may have a size ranging from one to five gallons or more. In one or more embodiments the lid may serve as a tray and further provide recessed surfaces for holding accessories in addition to one or more capsules.

The capsule and capsule lid may be comprised of a material suitable for long-term storage of biological agents and the capsule may be comprised of metal, plastics, flexible films, composite materials or combinations thereof.

The device may further comprise a handle for ease of transport of the device.

One embodiment of the device 10 is illustrated in FIGS. 1-5. The device 10 comprises a main body 12 and a lid 14 therefor. The main body 12 is a container portion having a floor and open top with a cavity 16 therein. The cavity 16 comprises a reservoir which may be considered a chamber for seed lubricant.

The lid 14 has a perimeter 22 which provides a lid for connection with the main body 12. The lid 14 supports one or more capsules, or chambers, 24 which are sealed capsules 24. In the embodiment illustrated, the lid 14 holds three capsules 24 and these capsules 24 are embedded or integral with the lid 14. Thus, the capsules 24 transcend the lid 14 and extend into the main body 12. However, the capsules 24 may alternatively be removably coupled to openings in the lid 14 while extending below the lid 14 into the main body 12 in a similar manner. The capsules 24 have one or more walls, a floor and a top such that the capsule 24 is a closed chamber which isolates the contents therein from the main body 12 and/or prevents mixing of the content of the capsule 24 with the contents of the main body 12 or chamber. The capsules 24 may be sealed as necessary to retain the contents in a viable state.

Each capsule 24 comprises one or more dividing members 32 which may be a wall(s) and/or floor(s) of the capsule 24 or portions thereof. Deployment of the contents of the chamber 24 into the main body comprises rupturing and/or displacing this dividing member 32. The one or more dividing members 32 may be made from the same or different material than a capsule lid 20 or other portions of the capsule 24 as the dividing member 32 is tearable, frangible, puncturable, rupturable, dissolvable, movable or combinations thereof.

The device 10 further comprises a deployment mechanism that is actuated to deploy the contents from one or more capsules 24 into the main body 12 of the device 10. This allows the contents of the capsule 24 to be stored long term and mixed with the contents of the main body 12 directly prior to applying the mixture to seed for planting. The deployment mechanism is a push-button 34 which can be manually depressed to effect rupture, tearing, puncture, dissolution, movement, opening and/or otherwise preventing the dividing member 32 from separating the contents of the capsule 24 from the main body 12. The deployment mechanism may comprise a plunger having a push-button 34 positioned on a top of each capsule 24 where the plunger may have an end extending into the capsule 24 and configured to puncture, tear, displace and/or otherwise break the dividing member 32.

Figures 6, 7:
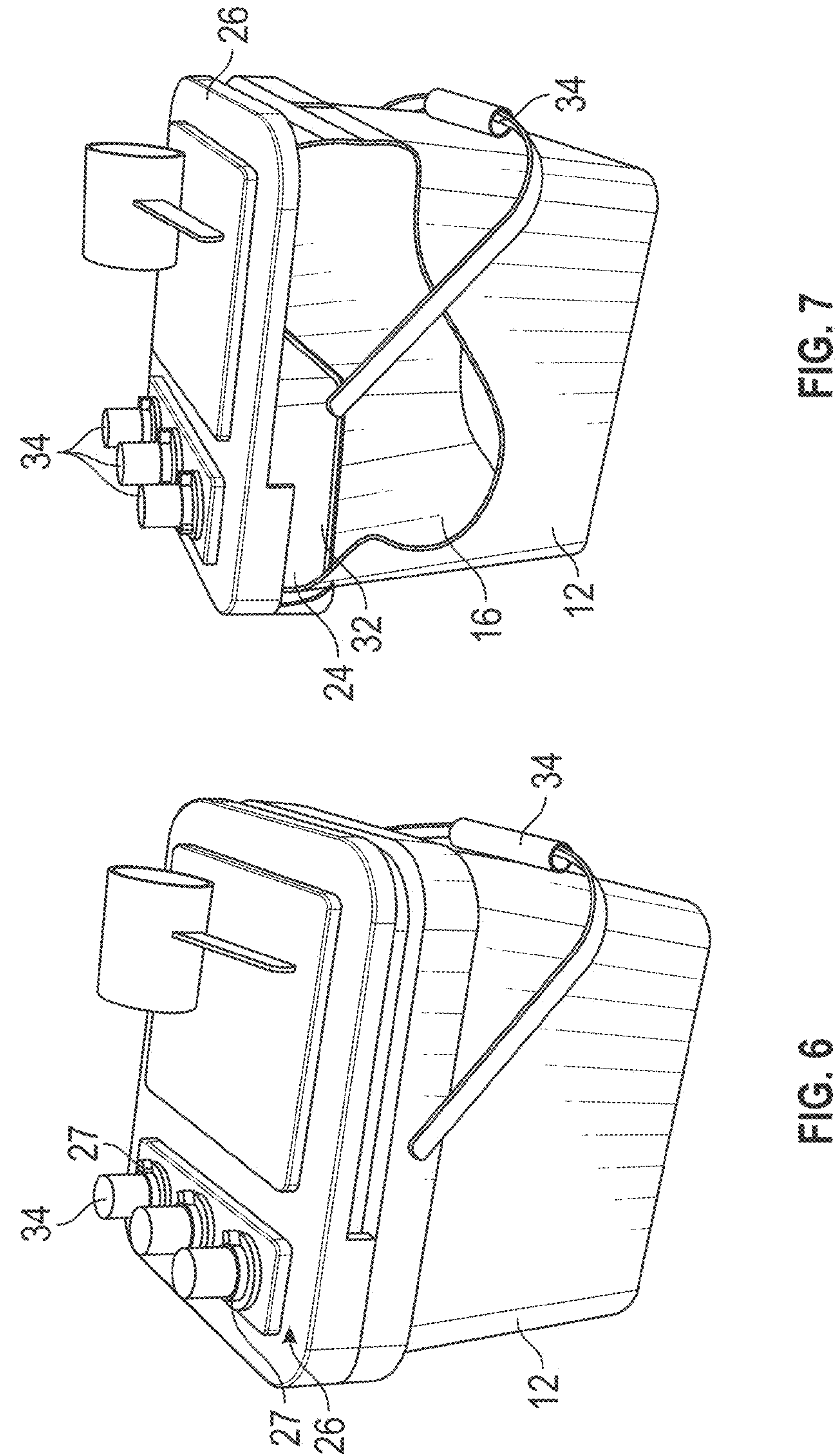
FIG. 6 is a side view of a package with a cover thereon according to one or more embodiments.
FIG. 7 is another side view of the package with cover and illustrating an interior of a main body of the package.

As illustrated in FIGS. 6 and 7, the lid 14 may further be provided with a cover 26 portion for covering a top of the capsules 24 held by the lid 14. The cover 26 provides openings 27 for exposing the deployment mechanisms which may be accessed and deployed while the device 10 is otherwise a closed device. The device 10 may also include a handle 44 for ease of transport. The device 10 may further be provided with a convenient scoop 42 for ease of removal of the seed lubricant and capsule contents after mixing for applying to seed.

While the embodiment illustrated in the figures supports one and three capsules respectively, the device may support one or more capsules including two capsules as well as up to six or more capsules. Each capsule may comprise one type of biological agent or a mixture thereof.

Dimensions and shapes of the capsules, main body, lid and/or cover are not limited to those illustrated in the figures and may vary depending on a quantity of seed lubricant with viable microorganisms desired.

Although the present disclosure has been described with reference to preferred embodiments, workers skilled in the art will recognize that changes may be made in form and detail without departing from the spirit and scope of the disclosure.

The invention claimed is:

1. A package comprising:

a main body storing a seed additive;

a lid removably coupled to the main body, the lid defining an opening and at least one chamber disposed within the opening, the chamber retaining microorganisms in a viable state;

a dividing member separating the main body and the chamber; and a disrupting mechanism that disrupts the dividing member such that the seed additive and the microorganisms form a mixture thereof.

2. The package of claim 1, wherein the at least one chamber is integrated into the lid.

3. The package of claim 1, wherein the dividing member is tearable, frangible, puncturable, rupturable, dissolvable, movable or a combination thereof.

4. The package of claim 1, wherein the disrupting member is manually actuated to disrupt the dividing member.

5. The package of claim 1, wherein the disrupting mechanism comprises a push-button on a top side of the chamber, the push-button accessible from above the lid when the chamber is disposed within the opening thereof, and wherein the push-button is operably connected to a plunger disposed within the chamber to move the plunger to tear, puncture, rupture, dissolve, or move the dividing member to release the microorganisms from the chamber.

6. The package of claim 1, wherein the seed additive is a seed lubricant comprising at least one of talc, graphite, wax, or polymer.

7. A package for delivering viable microorganisms to a seeder and/or planter, the package comprising:

a body portion comprising a first chamber storing a seed additive;

a lid portion coupled to the body portion, the lid portion defining an opening;

a capsule comprising a second chamber, the capsule positionable at least partially within the opening of the lid portion, wherein the second chamber contains microorganisms in a viable state;

a dividing member separating the microorganisms in the second chamber from the seed additive in the first chamber; and a deployment mechanism that disrupts the dividing member such that the microorganisms are released from the second chamber of the capsule and into the first chamber of the body portion, wherein the microorganisms are mixed into the seed additive forming a mixture thereof.

8. The package of claim 7, wherein the dividing member is tearable, frangible, puncturable, rupturable, dissolvable, movable or a combination thereof.

9. The package of claim 7, wherein the deployment mechanism is at least partially disposed within the second chamber, such that actuation of the disrupting mechanism disrupts the dividing member to release the microorganisms from the second chamber into the first chamber.

10. The package of claim 9, wherein the deployment mechanism comprises a push-button on a top side of the capsule, the push-button accessible from above the lid portion when the capsule is positioned within the opening thereof, and wherein the push-button is operably connected to a plunger disposed within the second chamber to move the plunger to tear, puncture, rupture, dissolve, or move the dividing member to release the microorganisms from the capsule.

11. The package of claim 7, wherein the seed additive is a seed lubricant comprising at least one of talc, graphite, wax, or polymer.

12. The package of claim 7, wherein the dividing member is a sealing member to seal the second chamber of the capsule when the dividing member is not disrupted.

13. The package of claim 7, wherein the capsule extends from a top side of the lid portion and into the body portion storing the seed additive therein, such that the deployment mechanism is accessible from outside the body portion and the microorganisms are released into the first chamber.

14. The package of claim 7, wherein the lid portion comprises one or more recessed surfaces for holding accessories or tools for transferring the mixture of the seed additive and the microorganisms from the first chamber to at least one of a planter box, a seed hopper, or a seed container for application to seeds.

15. The package of claim 7, wherein the lid portion defines a plurality of openings, and the package further comprises a plurality of capsules storing microorganisms therein, the plurality of capsules positionable within the plurality of openings.

16. A method of delivering viable microorganisms to a seeder and/or a planter, the method comprising:

providing a lid defining an opening, a capsule positionable in the opening, wherein the capsule comprises microorganisms within a first chamber at least partially defined by a disruptable dividing member;

attaching the lid to a container defining a second chamber, the container storing a medium to be delivered to the seeder and/or the planter, wherein the disruptable dividing member separates the microorganisms from the medium;

disrupting the disruptable dividing member via a disrupting mechanism to release the microorganisms from the capsule and into the medium stored within the container to form a mixture thereof, and applying the mixture of microorganisms and medium to seeds.

17. The method of claim 16, further comprising pushing a top portion of the capsule to move a plunger of the disrupting mechanism disposed inside the first chamber to disrupt the disruptable dividing member.

18. The method of claim 16, further comprising:

transporting and storing the container with the lid attached thereto and the capsule positioned within the opening of the lid, such that the microorganisms are separated from the mixture; and disrupting the disruptable dividing member after waiting until a time proximate planting of seeds via the seeder or the planter to mix the microorganisms and the medium.

19. The method of claim 18, disrupting the disruptable dividing member after waiting one or more days from storing the container to mix the microorganisms and the medium.

20. The method of claim 16, wherein the medium is a seed lubricant, and wherein the method further comprises depositing the mixture of microorganisms and seed lubricant into at least one of the seeder, the planter, or the seed container to apply the mixture to seeds stored therein.

* * * * *